United States Patent
Ledford et al.

(10) Patent No.: US 10,143,800 B2
(45) Date of Patent: Dec. 4, 2018

(54) FLUSHING A FLUID LINE FROM A MEDICAL PUMP

(71) Applicant: SMITHS MEDICAL ASD, INC., Rockland, MA (US)

(72) Inventors: Ricky L. Ledford, Brooklyn Park, MN (US); Sachin Kumar Choudhary, Santa Clara, CA (US); Lori Lynette Patoros, Simi Valley, CA (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 615 days.

(21) Appl. No.: 14/508,657

(22) Filed: Oct. 7, 2014

(65) Prior Publication Data

US 2015/0025453 A1     Jan. 22, 2015

Related U.S. Application Data

(62) Division of application No. 12/974,473, filed on Dec. 21, 2010, now Pat. No. 8,876,793.

(Continued)

(51) Int. Cl.
*A61M 5/168* (2006.01)
*A61M 5/14* (2006.01)
(Continued)

(52) U.S. Cl.
CPC ............ *A61M 5/1684* (2013.01); *A61M 5/14* (2013.01); *A61M 5/142* (2013.01); *A61M 5/168* (2013.01);
(Continued)

(58) Field of Classification Search
CPC .... A61M 5/1684; A61M 5/142; A61M 5/168; A61M 5/14; A61M 2005/1403; A61M 2039/0018
See application file for complete search history.

(56) References Cited

U.S. PATENT DOCUMENTS 3,858,581 A     1/1975 Kamen
4,227,526 A  *  10/1980 Goss ...................... A61M 1/16
                                        128/DIG. 13
(Continued)

FOREIGN PATENT DOCUMENTS

JP     H07503396 A    4/1995

OTHER PUBLICATIONS

Japan Patent Office, Official Action issued in Application No. 2013-531572 dated Apr. 27, 2015.
(Continued)

*Primary Examiner* — Bradley J Osinski
(74) *Attorney, Agent, or Firm* — Seager, Tufte & Wickhem, LLP

(57) ABSTRACT

A method and medical pump to perform a flushing procedure are provided. The medical pump is configured to execute the flushing procedure subsequent to an infusion procedure, the flushing procedure and infusion procedure lacking a specified relationship between each other until after performance of the infusion procedure. The method comprises performing an infusion procedure of a medicament with the medical pump and automatically querying in human detectable form whether to execute a flushing procedure in response to conclusion of the infusion procedure.

17 Claims, 8 Drawing Sheets

Related U.S. Application Data

(60) Provisional application No. 61/388,955, filed on Oct. 1, 2010.

(51) Int. Cl.
*A61M 5/142* (2006.01)
*A61M 39/00* (2006.01)

(52) U.S. Cl.
CPC ............... *A61M 2005/1403* (2013.01); *A61M 2039/0018* (2013.01)

(56) References Cited

U.S. PATENT DOCUMENTS

| | | | |
|---|---|---|---|
| 4,563,175 A * | 1/1986 | LaFond | A61M 5/1456 128/DIG. 12 |
| 4,828,545 A * | 5/1989 | Epstein | A61M 5/14224 604/66 |
| 4,857,056 A | 8/1989 | Talonn | |
| 4,935,009 A | 6/1990 | Caldwell et al. | |
| 4,966,579 A * | 10/1990 | Polaschegg | A61M 5/16831 604/131 |
| 5,649,810 A | 7/1997 | Schweitzer, Jr. et al. | |
| 6,500,156 B1 | 12/2002 | Stansbury | |
| 2004/0039344 A1 | 2/2004 | Baldwin et al. | |
| 2007/0233004 A1* | 10/2007 | Sims | A61M 5/1454 604/152 |
| 2008/0119822 A1 | 5/2008 | Knauper | |

OTHER PUBLICATIONS

International Search Report and Written Opinion from counterpart PCT/US2011/043684 dated Aug. 16, 2011 (10 pages).

U.S. Patent and Trademark Office, Office Action issued in corresponding U.S. Appl. No. 12/974,473, dated May 10, 2013, 10 pages.

U.S. Patent and Trademark Office, Final Office Action issued in corresponding U.S. Appl. No. 12/974,473, dated Nov. 29, 2013, 13 pages.

U.S. Patent and Trademark Office, Advisory Action issued in corresponding U.S. Appl. No. 12/974,473, dated Jan. 27, 2014, 4 pages.

* cited by examiner

FLUSHING A FLUID LINE FROM A MEDICAL PUMP

CROSS-REFERENCE TO RELATED APPLICATION

This application is a divisional of U.S. patent application Ser. No. 12/974,473 entitled "FLUSHING A FLUID LINE FROM A MEDICAL PUMP" and filed on Dec. 21, 2010, which application claims the benefit of U.S. Patent Application No. 61/388,955 filed on Oct. 1, 2010. Each application is incorporated by reference in its entirety herein.

TECHNICAL FIELD

The present invention relates to medical pumps, and more particularly to flushing a fluid line between the medical pump and a patient.

BACKGROUND

Medical pumps (examples of which are syringe pumps, IV pumps, LVP pumps, peristaltic pumps, and implantable pumps) provide medicament to a patient through a fluid line during an infusion procedure. However, when an infusion procedure is complete, some of the medicament may remain in the fluid line. If the fluid line is removed for disposal, the medicament left in the fluid line is wasted. It is also possible, in those situations, that the patient will have received less medicament than intended.

In other situations, the fluid line may be left in place for a subsequent infusion procedure. That subsequent infusion procedure results in pushing the remaining medicament into the patient, which may occur at a time when the patient should not get that medicament and without steps being taken to include that amount in the determination of how much of a specific medicament a patient received. Furthermore, the medicament of the second infusion procedure may undesirably mix with the remaining medicament from the prior infusion procedure. To avoid the problem, in such situations, the fluid line may be flushed with a flushing fluid, such as saline, between infusion procedures. The solution used to flush the tubing varies depending upon institutional and standard protocol, however.

One flushing method is to manually clear the fluid line with an infusion of saline therethrough. The manual method has the disadvantage that an incorrect amount of saline may be infused such that the fluid line is either not properly cleared of the medicament or saline is unnecessarily infused into the patient. The rate that the saline is infused might also not match well to the rate at which the medicament was infused creating a risk of side effects, such as might occur with a rapid manual flush. The inability to accurately determine the amount of remaining medicament infused into the patient presents the further drawback that the amount of actual medicament infused into the patient cannot be easily tracked by the medical pump.

To reduce the problems with manual flushing, the medical pump can be used to perform a second infusion-like procedure with a supply of flushing fluid rather than a medicament, such that a flushing procedure is implemented by the medical pump. In that regard, the clinician preprograms the flushing procedure with the programming of the first infusion procedure for the medicament such that the flushing procedure and infusion procedure have a specified relationship prior to the infusion procedure being performed. While that has the advantage that the flushing procedure can be preprogrammed with a precise amount of saline to be infused sufficient to properly clear the fluid line, there are some drawbacks to preprogramming an infusion procedure. For example, the medical pump is tracking the volume of medicament infused, stops tracking when the first infusion procedure ends, and starts tracking the volume infused anew when the flushing procedure begins. As a consequence, the amount of medicament infused is not accurately tracked, thus presenting some of the same drawbacks associated with the manual flushing procedure. Preprogramming the pump also presents potential for confusion when the flushing procedure is to be implemented.

SUMMARY

The present invention provides a mechanism for automatically assisting clinicians in using a medical pump when flushing a fluid line as desired without the need to preprogram the medical pump, thus avoiding the drawbacks thereof, while also avoiding the drawbacks of manual flushing. To that end, and in accordance with a principle of the present invention, after completion of a medicament infusion procedure, the medical pump automatically queries in a human detectable form whether a flushing procedure is to be performed, the flushing procedure lacking a specified relationship with the infusion procedure until after performance of the infusion procedure. That query may, for example, be in the form of a message on a display such as of the medical pump, or may be an aurally perceptible message played by or in response to signals from the medical pump. In some instances a clinician will choose not to perform a flushing procedure. However, where a flushing procedure is to be performed, the automatic query serves as a current reminder for the clinician to program the pump for the flushing procedure and properly set up the medical pump for the flushing procedure at that time such that any relationship between the infusion procedure and the flushing procedure is specified after the infusion procedure. Thus, there is no requirement that the clinician preprogram the medical pump with a flushing procedure having a specified relationship with the infusion procedure, such that the risk of confusion created by preprogramming is minimized or eliminated.

In accordance with a second principle of the present invention, the medical pump is configured to track the volume of fluid expelled by the medical pump both during an infusion procedure as well as during the subsequent flushing procedure, all without losing track of the amount of medicament infused. To that end, in accordance with one aspect of the present invention, the medical pump includes in the volume of medicament infused the volume of fluid expelled by the medical pump during the flushing procedure. As a consequence, the medical pump more accurately tracks the true volume of medicament infused to the patient. The medical pump may also advantageously separately track the volume of fluid expelled by the medical pump during the flushing procedure.

Situations can arise where the flushing procedure stops, which in some cases may occur before the flushing procedure is concluded. To that end, and in accordance with a third principle of the present invention, the medical pump is configured to determine when a flushing procedure has been stopped, and to automatically query in a human detectable form whether to cancel the flushing procedure or restart the flushing procedure. Where the clinician elects to restart the flushing procedure, the medical pump may advantageously provide the opportunity for the clinician to adjust the settings of that flushing procedure. As a consequence, the clinician is presented the opportunity to adjust a flushing procedure mid-course.

By virtue of the foregoing, there is thus provided a mechanism for automatically assisting clinicians in using a medical pump when flushing a fluid line as desired without the need to preprogram the medical pump, thus avoiding the drawbacks thereof, while also avoiding the drawbacks of manual flushing. These and other advantages of the present invention shall be made apparent from the accompanying drawings and detailed description thereof.

BRIEF DESCRIPTION OF THE DRAWINGS

The accompanying drawings, which are incorporated in and constitute a part of this specification, illustrate aspects of the present invention and, together with a general description of the invention given above and the detailed description of the drawings given below, serve to explain the principles of the invention.

DETAILED DESCRIPTION OF THE DRAWINGS

Figure 1:
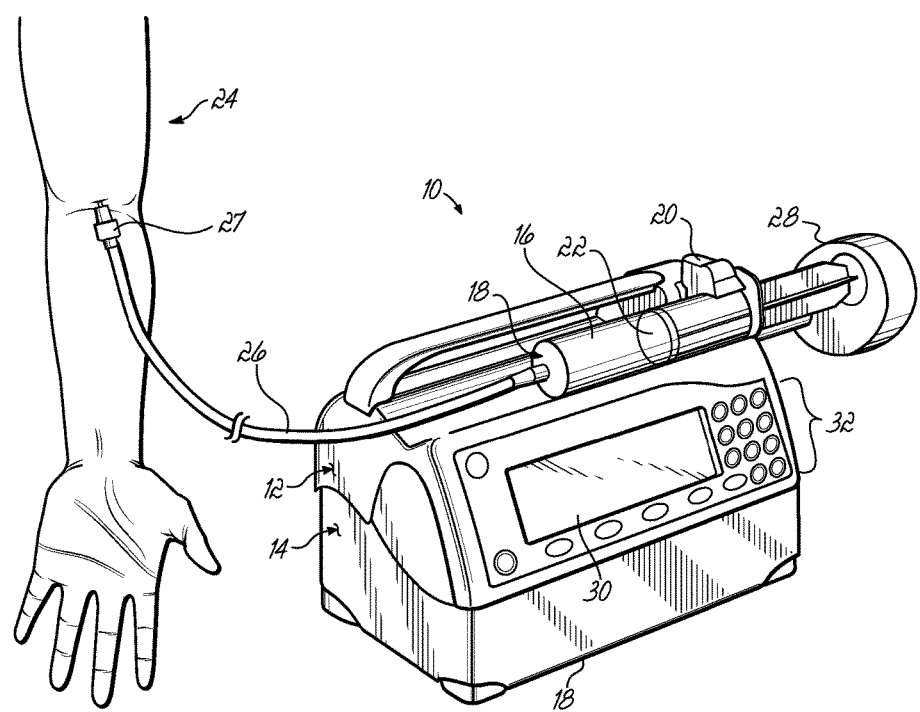
FIG. 1 is perspective illustration of an exemplary medical pump, in the form of a syringe pump, configured with automatic query features related to a flushing procedure for purposes of explaining the principles of the present invention.

With reference to FIG. 1 there is shown in perspective view a medical pump 10, in the form of a syringe pump 10, configured with automatic query features according to the principles of the present invention. While the following description is thus provided in the context of the exemplary syringe pump 10, one of ordinary skill in the art will appreciate that the automatic query features related to a flushing procedure of the present invention may be applied to other medical pumps which expel medicaments into a fluid line for infusion into a patient. The syringe pump 10 includes a head 12 and a base 14. As illustrated in FIG. 1, the syringe pump 10 is configured to infuse the fluid contents of a syringe 16 via a fluid line 26 to a patient 24 such as through a catheter 27. Syringe 16 includes a barrel 18 supported on the head 12 of the syringe pump 10 and secured by a clamp 20. The clamp 20 is coupled to a sensor 62 (FIG. 2), which is typically internal to the head 12, to determine the outer diameter of the syringe 16. The syringe 16 includes a plunger 22 extending therein and moveable within the barrel 18 to expel the fluid contents into the fluid line 26.

To this end, a stepper motor 58 (FIG. 2) internal to the housing head 12 actuates a piston drive 28 to move the plunger 22. A sensor 62 (FIG. 2) monitors the force exerted by the piston drive 28 to determine the fluid force of the fluid upon the patient 24. The piston drive 28 drives the fluid out of the syringe 16 into the downstream fluid line 26 at a controlled rate based on parameters programmed into the syringe pump 10 including certain parameters related to the physical characteristics of the syringe 16. The barrel 18 of the syringe 16 is retained so as to allow the plunger 22 to be pushed by the piston drive 28 such as by means of a slot to hold at least a portion of the barrel 18. The plunger 22 may be retained by a forward facing surface of the piston drive 28 that clamps the base of the plunger 22 thereto.

As illustrated in FIG. 1, the head 12 includes a display 30 and an operator interface 32 comprised of a plurality of switches or the like. The display 30 may display options for a clinician (not shown) to choose through the operator interface 32. Input from the clinician may include selecting various menu items, including selecting various programs and/or profiles, as well as data pertaining to characteristics of an infusion procedure or a flushing procedure, and data entry, all of which may be via operator interface 32.

Figure 2:
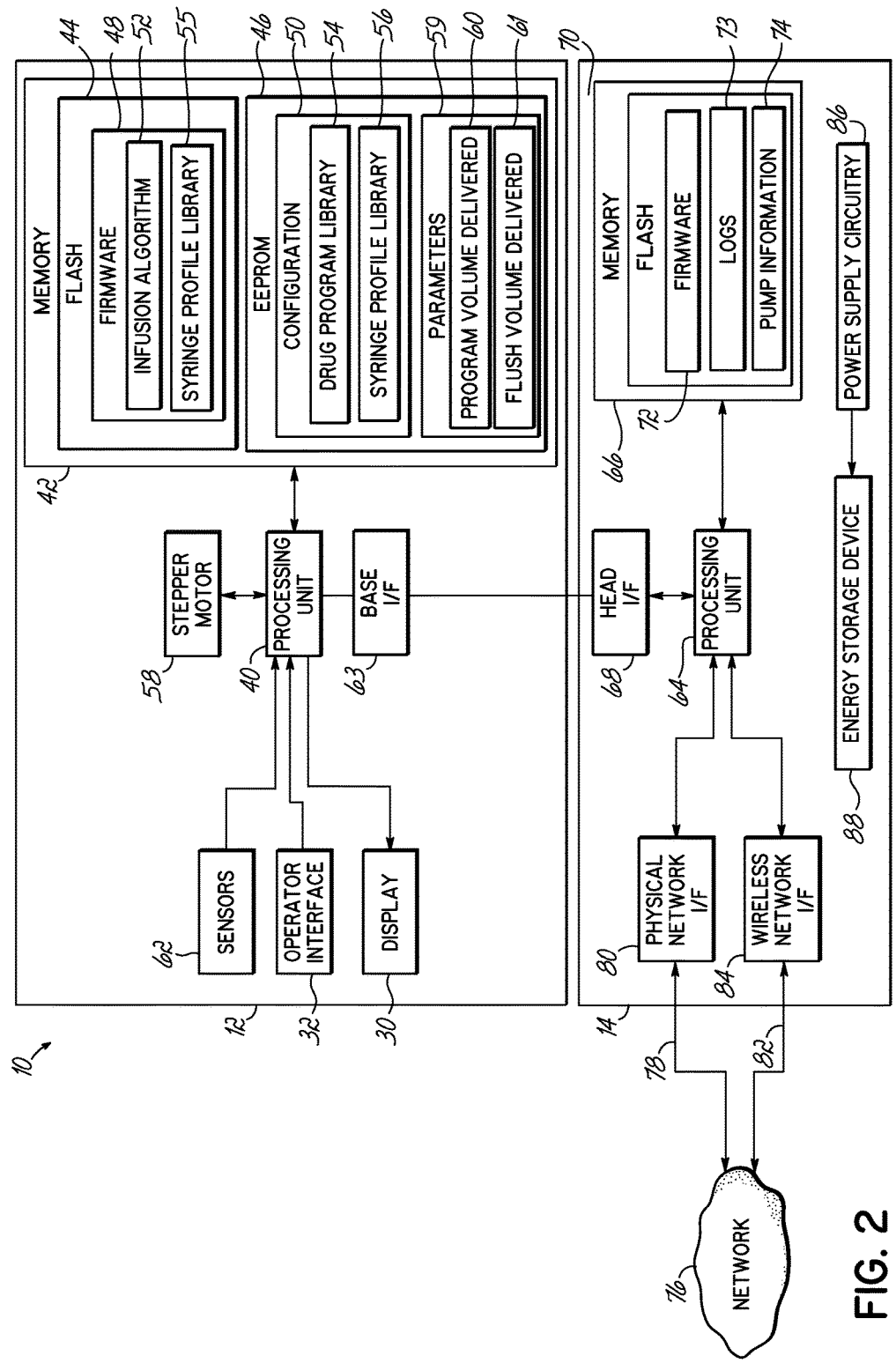
FIG. 2 is a diagrammatic illustration of the hardware and software components of the medical pump of FIG. 1.
Figure 3A:
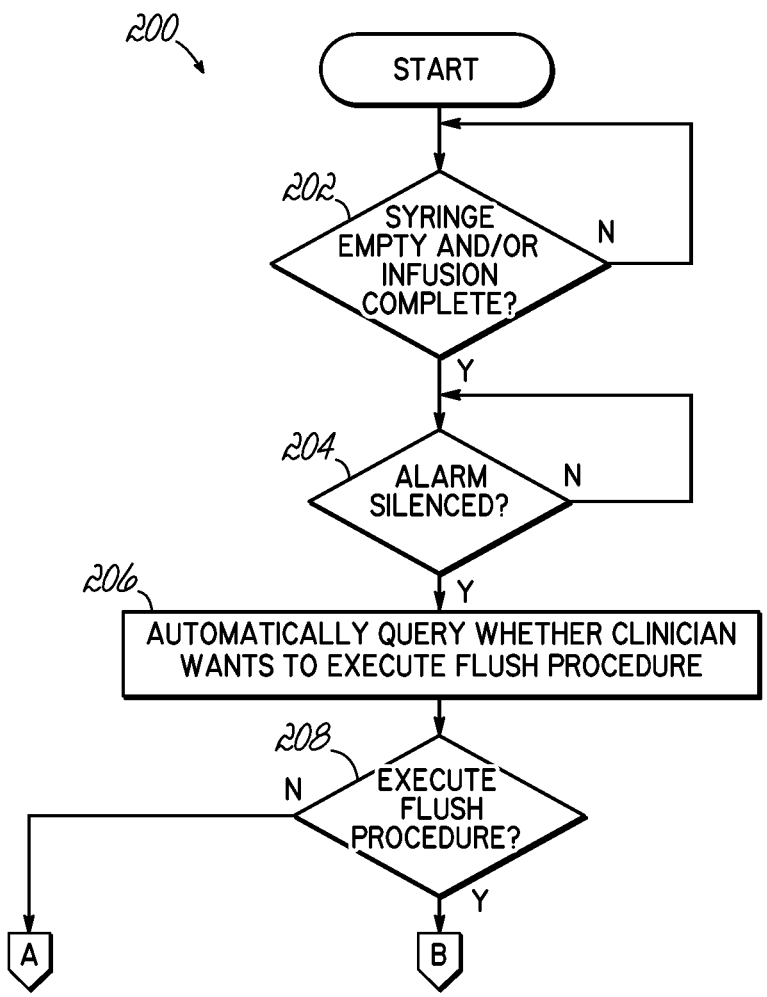
FIGS. 3A-3D is a flowchart illustrating a sequence of operations executable by the medical pump of FIG. 1 to automatically query in a human detectable form whether a flushing procedure is to be performed and to perform that flushing procedure.
Figure 3B:
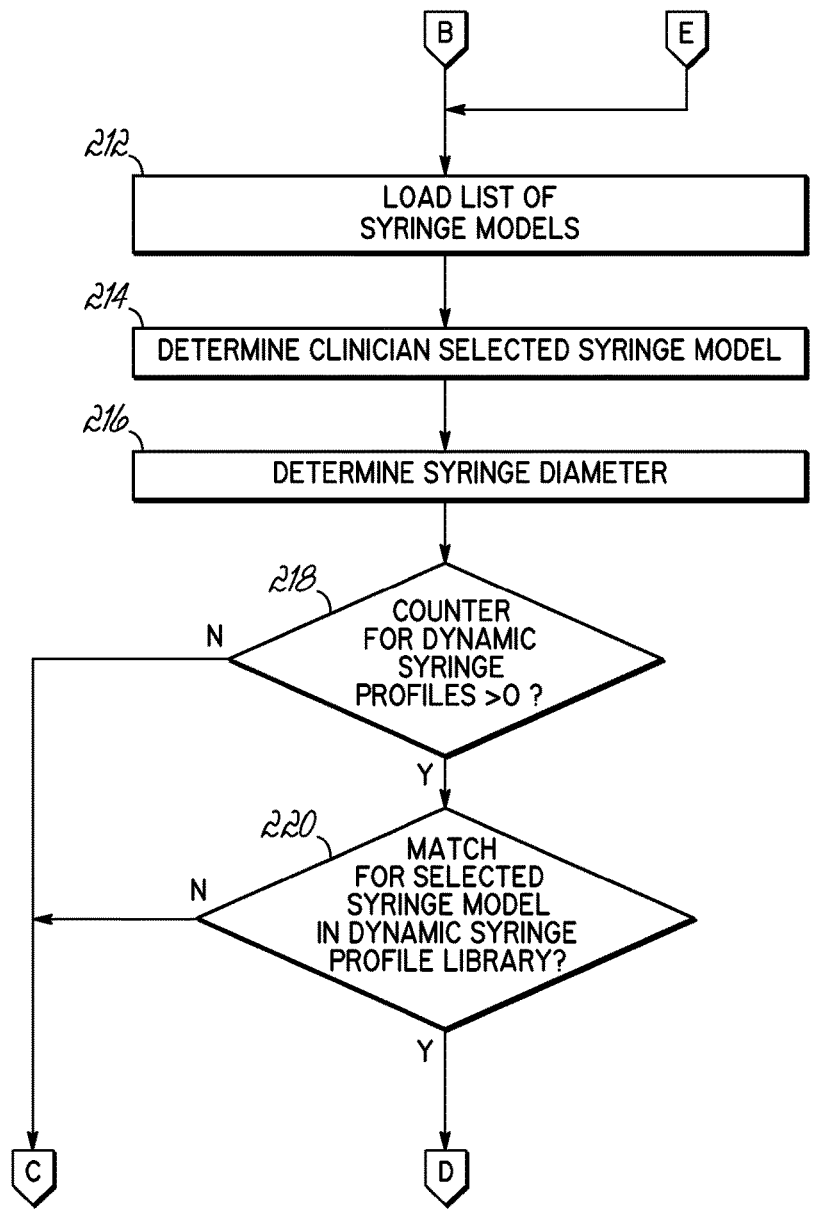
Figure 3C:
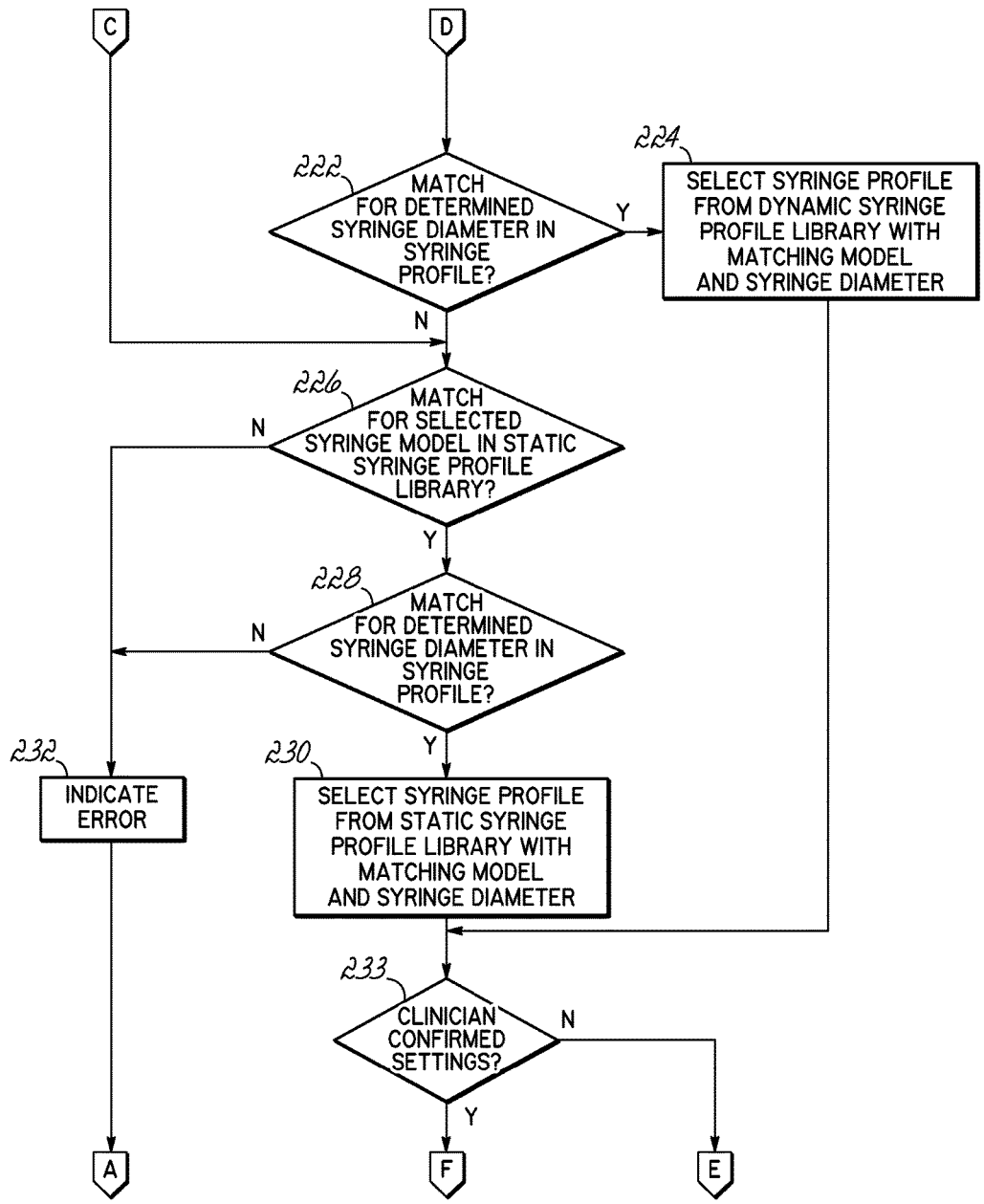
Figure 3D:
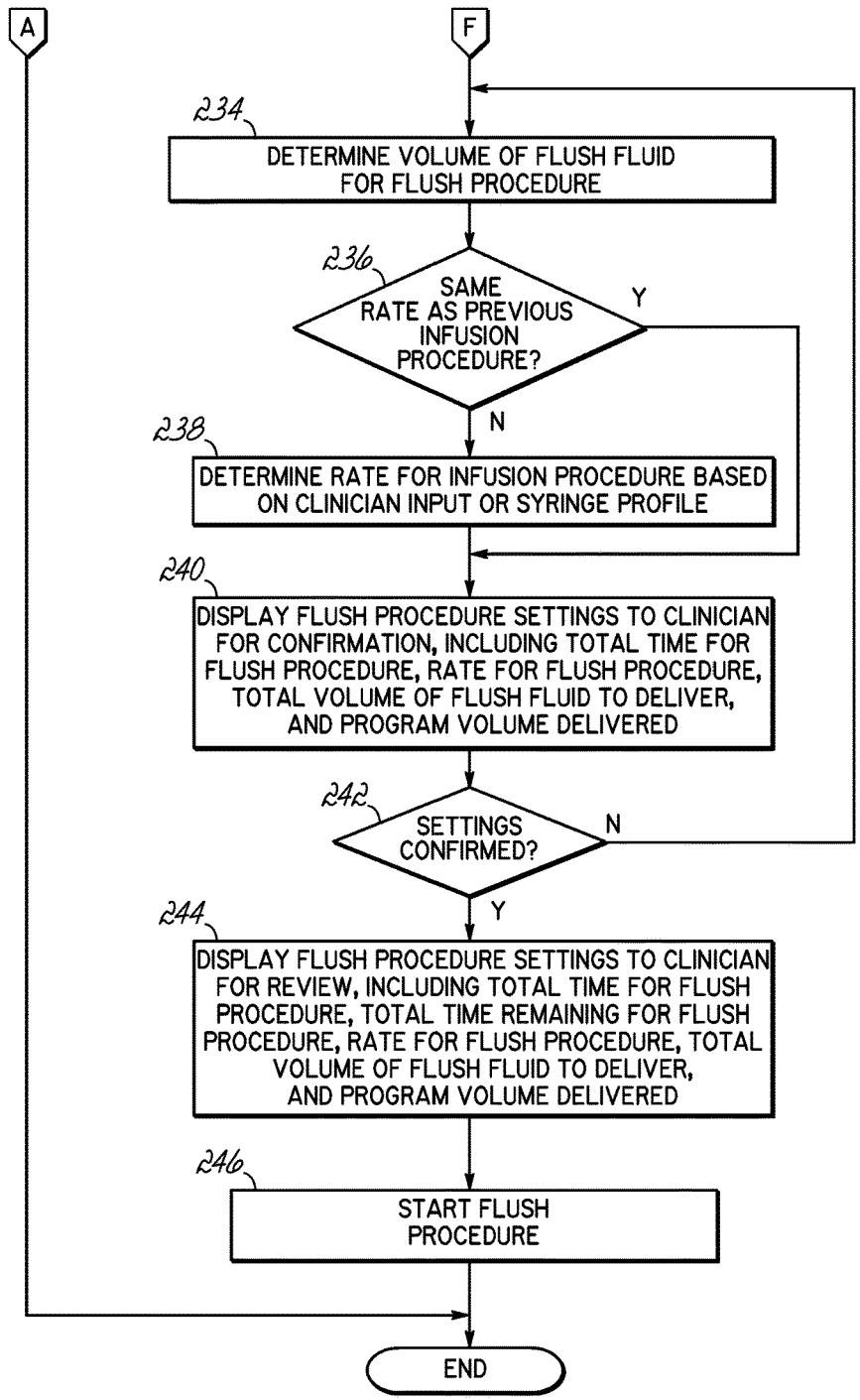

FIG. 2 illustrates a hardware and software environment for the syringe pump 10, and particularly the head 12 and base 14 thereof. The head 12 includes a head processor 40 coupled to a head memory 42. The head processor 40 is typically implemented in hardware using circuit logic disposed in one or more physical integrated circuit devices, or chips, and may be comprised of one or more microprocessors, micro-controllers, field programmable gate arrays, or ASICs. Head memory 42 may include a plurality of types of memory, including a flash memory 44 and an electronically erasable programmable read-only memory 46 (illustrated as, and hereinafter, "EEPROM" 46). As such, head memory 42 may be considered to include memory storage physically located elsewhere in the head 12 (e.g., any cache memory in the head processor 40, as well as flash memory 44, EEPROM 46, and any additional memory in the head 12). Similarly to each head processor 40, head memory 42, flash memory 44, and EEPROM 46 are also typically implemented using circuit logic disposed on one or more physical integrated circuit devices, or chips.

As illustrated in FIG. 2, the flash memory 44 is configured to contain firmware 48 for the head 12 while the EEPROM 46 is configured to contain configuration data 50. The firmware 48 includes data to control the components of the head 12 as well as an infusion algorithm 52. The infusion algorithm 52 is executed by the head processor 40 to determine a distance to move the plunger 22 of the syringe 16 over a time to achieve a desired rate or rates at which fluid is to be expelled from the syringe 16. By way of example, the distance-over-time to move the piston drive 28 to achieve a desired rate may be determined with respect to a syringe profile selected from at least one syringe profile library 55 in the firmware 48 (referred to herein as a static syringe profile library 55), a syringe profile selected from at least one syringe profile library 56 in the configuration data 50 (referred to herein as a dynamic syringe profile library 56), a drug program selected from at least one drug program library 54 in the configuration data 50 which identifies a syringe profile (which can be in either the dynamic syringe profile library 56 or the static syringe profile library 55), and data input by the clinician through the operator interface 32. The dynamic syringe profile library 56 is generally an additional and more easily changeable syringe profile library in the configuration data 50 than the static syringe profile library 55 in the firmware 48, and is thus referred to as the "dynamic" syringe profile library 56.

Utilizing the foregoing, the head processor 40 determines the necessary commands to operate the stepper motor 58 to control the piston drive 28 coupled to thereto in a manner to expel the appropriate amount of fluid from the syringe 16. Where a medicament is to be expelled, the procedure is considered an infusion procedure, whereas use of a flushing fluid, such as saline, is considered a flushing procedure. The EEPROM 46 may also include a parameters section 59 that stores parameters associated with the syringe pump 10, such as a program volume delivered identifier 60 to track the total volume of fluid medicament expelled from the syringe 16 during an infusion procedure as well as the volume of flushing solution expelled from a syringe 16 during a subsequent flushing procedure so as to provide a total volume of medicament infused into the patient 24 during both the infusion procedure and the subsequent flushing procedure. The EEPROM 46 may also include a flush volume delivered identifier 61 to separately track the volume of fluid expelled during the flushing procedure.

With respect to the drug program library 54, each drug program therein is associated with custom infusion parameters which contain specific information about modes of operation used in the syringe pump 10, are associated with specific syringe profiles, and are used by the head processor 40 to determine how to operate the stepper motor 58 and piston drive 28 to infuse the fluid contents of the syringe 16. By way of example, a drug program may include a name that specifies the particular fluid that is to be infused by that drug program, the particular syringe profile to use with that drug program, as well as the mode of infusion to use in the procedure for expelling that particular fluid. The modes of infusion may include a continuous mode (a continuous infusion of a specific flow rate in ml/hr with regard to volume limits, loading dose or bolus dose, the bolus dose being an optional parameter to specify a bolus volume to be delivered over a specified time, the loading dose being an optional parameter to use a specified volume as a one-time-only bolus prior to the start of normal delivery, and the volume limit being an optional parameter in which the pump stops or enters a "Keep Vein Open" rate once a specified volume has been reached), a body weight infusion mode (that may be programmed by drug concentration, patient weight or drug dosage, in which the pump calculates the correct flow rate in ml/hr to achieve a specified drug dose with regard to volume limit, loading dose or bolus dose), a volume-over-time infusion mode (in which the pump calculates the flow rate for a dose volume over a delivery time in ml/hr without regard to volume limit, loading dose or bolus dose), and an intermittent volume-over-time mode (in which the clinician specifies a delivery volume for a specific delivery time, after which the delivery stops for a programmed interval, with the pattern repeating without regard to volume limit, loading dose or bolus dose), to name a few examples. After an infusion procedure, the syringe pump 10 may automatically query a clinician in a human detectable form, such as by text or images on the display 30, whether to flush the fluid line 26 of the medicament remaining in the fluid line 26. When the clinician selects to flush the fluid line 26, such as by actuation of appropriate ones of the switches of the operator interface 32, the syringe pump 10 may determine parameters for, and implement, a flushing procedure in much the same way as done for an infusion procedure, only using a flushing solution, such as in a second syringe (not shown).

With respect to the syringe profile libraries 55 and 56, each syringe profile therein contains characterization information (about a respective syringe 16, e.g., physical measurements of the respective syringe 16) and/or identification information that is used by the head processor 40 to determine how to operate the stepper motor 58 and piston drive 28 to expel the fluid contents of the syringe 16. For example, a syringe profile may include a model name that specifies the particular model and/or manufacturer of a syringe 16 that is to be used, as well as a specific volume for that syringe 16 and physical measurements associated with the syringe 16. Each syringe profile also includes information that is utilized to display an identification of a syringe 16 (e.g., the manufacturer and model of a syringe 16) on the display 30 of the syringe pump 10 and is further utilized by the syringe pump 10 to calculate and/or determine, during an infusion procedure for example, when the syringe 16 is empty.

With respect to the program volume delivered identifier 60, that identifier is used to track the total volume of fluid expelled during an infusion procedure as well as any subsequent flushing procedure. As such, the syringe pump 10 periodically updates the program volume delivered identifier 60 during an infusion procedure and a subsequent flushing procedure such that the program volume delivered identifier 60 indicates the total amount of medicament infused into the patient 24 (which is the sum of the amount of medicament expelled during the infusion procedure and the amount of flushing fluid expelled during the flushing procedure as the latter pushes the remaining medicament along the fluid line 26 toward the patient 24 for infusion). The flush volume delivered identifier 61, on the other hand, is used to track the total amount of flushing fluid expelled during a flushing procedure. Thus, and again, the syringe pump 10 periodically updates the flush volume delivered identifier 61 during a flushing procedure such that the flush volume delivered identifier 61 indicates the total amount of flushing fluid expelled into the fluid line 26. The syringe pump 10 may advantageously update the program volume delivered identifier 60 and/or the flush volume delivered identifier 61 about every half-second during the infusion procedure and/or flushing procedure, as applicable.

The head processor 40 is further coupled to the display 30 as well as the operator interface 32. The head processor 40 is also coupled to a plurality of sensors 62. For example, the plurality of sensors 62 may include any or all of a force transducer sensor to indicate the force exerted on the plunger 22 of a syringe 16, a syringe plunger loaded sensor to indicate that the plunger 22 of the syringe 16 is loaded on the piston drive 28, a plunger travel sensor to indicate the distance traveled by the plunger 22 of the syringe 16, a syringe size sensor coupled to the clamp 20 to indicate the size of the syringe 16, and a motor rotation sensor to indicate rotation of the stepper motor 58 and the amount thereof. The head processor 40 is coupled to a base interface 63 (illustrated as "base I/F" 63) to interface with the base 14.

Turning to the base 14, the base 14 includes at least one base processing unit 64 coupled to a base memory 66 and a head interface 68 (illustrated as "head I/F" 68) to interface with the base interface 63 of the head 12. Each base processing unit 64 is also typically implemented in hardware using circuit logic disposed in one or more physical integrated circuit devices, or chips. Each base processing unit 64 may also be one or more microprocessors, micro-controllers, field programmable gate arrays, or ASICs, while base memory 66 includes a flash memory 70, and is also typically implemented using circuit logic disposed on one or more physical integrated circuit devices, or chips. It will be appreciated by a person having ordinary skill in the art that base memory 66 may be considered to include memory storage physically located elsewhere in the base 14 (e.g., any cache memory in the at least one base processing unit 64 and any additional memory in the base 14).

The flash memory 70 is configured to store the firmware 72 for the base 14 as well as at least one log 73 that stores data generated by the head 12 and base 14 and a pump information data structure 74. The pump information data structure 74 is configured to store information about the syringe pump 10, such as any or all of an indication of the particular revision of the firmware or configuration data installed on the syringe pump 10, a data structure identifier for the syringe pump 10 that indicates the particular data structure used by the syringe pump 10 to store information, and a component identifier that indicates the particular hardware configuration of the syringe pump 10.

The base 14 is configured to couple to a network 76 through a cable as at 78 with a wired network interface 80 (illustrated as "wired network I/F" 80) coupled to the base processing unit 64. Alternatively, the base 14 may be configured to couple to the network 76 through a wireless signal as at 82 with a wireless network interface 84 (illustrated as "wireless network I/F" 84) coupled to the base processing unit 64. In this manner, the base 14 is configured to communicate across the network 76 to send and receive data, such as to or from a computer system or server (both not shown). The base 14 also includes power supply circuitry 86 to convert AC power to DC power for the head 12 and base 14 when the base 14 is coupled to an AC power source (not shown), as well as an energy storage device 88 to supply DC power to the head 12 and base 14 when the base 14 is not coupled to the AC power source.

The routines executed to implement the present invention, whether implemented as part of an operating system or a specific application, component, program, object, module or sequence of instructions executed by a syringe pump 10 will be referred to herein as a "sequence of operations," a "program product," or, more simply, "program code." The program code typically comprises one or more instructions that are resident at various times in various memory and storage devices, and that, when read and executed by one or more processors, such as head processor 40, of syringe pump 10, cause that syringe pump 10 to perform the steps necessary to execute steps, elements, and/or blocks embodying the various aspects of the invention by thus using the processor(s).

While the invention has and hereinafter will be described in the context of a fully functioning syringe pump 10, a person having ordinary skill in the art will appreciate that the various aspects of the present invention are capable of being distributed as a program product in a variety of forms, and that the invention applies equally regardless of the particular type of computer readable signal bearing media used to actually carry out the distribution. Examples of computer readable signal bearing media include but are not limited to physical and tangible recordable type media such as volatile and nonvolatile memory devices, floppy and other removable disks, hard disk drives, optical disks (e.g., CD-ROM's, DVD's, etc.), among others, and transmission type media such as digital and analog communication links.

In addition, various program code described hereinafter may be identified based upon the application or software component within which it is implemented in. However, it should be appreciated that any particular program nomenclature that follows is used merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, APIs, applications, applets, etc.), it should be appreciated that the invention is not limited to the specific organization and allocation of program functionality described herein.

The automatic query feature of the present invention provided to avoid the drawbacks of preprogramming a flushing procedure will now be described by reference to the flowchart 200 of FIGS. 3A-3D which illustrates a sequence of operations for the syringe pump 10 to automatically assist clinicians in using the syringe pump 10 for a flushing procedure without the need to preprogram that flushing procedure with a specified relationship to an infusion procedure. Furthermore, the flowchart 200 of FIGS. 3A-3D illustrates that the sequence of operations for the syringe pump 10 allows the head processor 40 to select a syringe profile from the dynamic syringe profile library 56 or the static syringe profile library 55. The head processor 40 initially determines whether a syringe 16 is empty and/or an infusion procedure has completed (block 202). When a syringe 16 is not empty and/or an infusion procedure has not completed ("No" branch of decision block 202), the sequence of operations returns back to block 202. However, when a syringe 16 is empty and/or an infusion procedure has completed ("Yes" branch of decision block 202), the head processor 40 determines whether a clinician has silenced an alarm associated with that empty syringe 16 and/or completed infusion procedure (block 204). When the alarm has not been silenced (i.e., when the clinician has not yet acknowledged the alarm) ("No" branch of decision block 204), the sequence of operations returns back to block 204. However, when the alarm has been silenced ("Yes" branch of decision block 204), the head processor 40 automatically queries, in a human detectable form, whether the clinician wants to execute a flushing procedure (block 206). At that point, the flushing procedure lacks a specified relationship with the infusion procedure.

By way of example, the query may be in the form of a message on a display 30 of the syringe pump 10. The message may also provide legends relative to various of the operator interfaces 32 to thus make them "soft keys." By selective actuation thereof, the clinician instructs the syringe pump 10 to proceed with an infusion procedure, for example, or of the election not to undertake an infusion procedure. Additionally or alternatively, the human detectable form of query may be an aurally perceptible message played through a speaker (not shown) of the syringe pump 10 and/or elsewhere in response to signals from the syringe pump 10, such as may be transmitted over the network 76.

In response to clinician input with operator interface 32 as to how to proceed (e.g., whether to execute a flushing procedure or not), the head processor 40 determines whether the clinician has chosen to execute a flushing procedure (block 208). When the clinician has not chosen to execute a flushing procedure ("No" branch of decision block 208), the sequence of operations may end. However, when the clinician has chosen to execute a flushing procedure ("Yes" branch of decision block 208), the head processor 40 loads a list of syringe models for syringe profiles in the memory 42 and/or 66 of the syringe pump 10 (e.g., a list of syringe models of corresponding profiles in the dynamic syringe profile library 56 and the static syringe profile library 55) (block 212). The head processor 40 determines a syringe model selected by the clinician (block 214) and determines the outer diameter of the syringe 16 with a sensor 62 coupled to a clamp 20 of the syringe pump 10 when that syringe 16 is loaded (block 216).

After determining a selected model (block 214) and determining the diameter of the syringe 16 (block 216), the head processor 40 determines whether a counter indicates that the number of syringe profiles in the dynamic syringe profile library 56 is greater than zero (block 218). When the counter is greater than zero ("Yes" branch of decision block 218), the head processor 40 determines whether there is a match for the selected syringe model in a syringe profile of the dynamic syringe profile library 56 (block 220). When there is a match for the selected syringe model in a syringe profile of the dynamic syringe profile library 56 ("Yes" branch of decision block 220), the head processor 40 goes on to determine whether there is a match for the determined syringe diameter in the syringe profile (block 222). By way of example, each syringe profile may include an indication of at least one range for a syringe diameter for which that syringe profile may be used. The range allows for compensation of material and/or manufacturing variances in a particular type and/or size of syringe. Such variances can arise because the actual diameter of a syringe 16 may differ slightly from its declared diameter. For example, material and/or manufacturing variances in a syringe 16 with a declared outer diameter of 60 mm may result in that syringe 16 having an actual outer diameter of 59.9 mm or 60.1 mm. As such, the determined syringe diameter matches or corresponds to a range for a syringe diameter when the determined syringe diameter falls within that range.

Thus, when there is a match for the determined syringe diameter in the syringe profile ("Yes" branch of decision block 222), the head processor 40 selects that syringe profile from the dynamic syringe profile library 56 that includes the matching model and matching syringe diameter (block 224). However, when the counter is not greater than zero, which is typically indicated by the counter being zero ("No" branch of decision block 218), when there is not a match for the selected syringe model in a syringe profile of the dynamic syringe profile library 56 ("No" branch of decision block 220), or when there is not a match for the determined syringe diameter in an otherwise matching syringe profile in the dynamic syringe profile library 56 ("No" branch of decision block 222), the head processor 40 determines whether there is a match for the selected syringe model in a syringe profile of the static syringe profile library 55 (block 226).

Alternatively, the counter evaluated in block 218 may not indicate the number of syringe profiles in the dynamic syringe profile library 56, but may instead include a flag indicating whether the dynamic syringe profile library 56 includes one or more syringe profiles. As such, the sequence of operations of FIGS. 3A-3D may include, at block 218, a decision block to determine whether the dynamic syringe profile 56 includes any syringe profiles based upon that flag. To illustrate one example, the flag may be set when the dynamic syringe profile library 56 includes one or more syringe profiles, but cleared when the dynamic syringe profile 56 does not include any syringe profiles or does not exist. As such, the determination in block 218 may be replaced by a determination of whether the flag is set. Thus, when the flag is set (which, in this example, would correspond to the "Yes" branch of decision block 218), the sequence of operations proceeds to block 220. However, when the flag is not set or clear (which, in this example, would correspond to the "No" branch of decision block 218), the sequence of operations proceeds to block 226.

Further alternatively, the counter evaluated in block 218 may include a number that does not indicate the actual number of syringe profiles in the dynamic syringe profile library 56, but is instead used to indicate that there is one or more syringe profile in the dynamic syringe profile library 56 when that number is greater than zero. To illustrate another example, the counter may be greater than zero when the dynamic syringe profile library 56 includes one or more syringe profiles, but zero or negative when the dynamic syringe profile 56 does not include any syringe profiles or does not exist. With respect to the sequence of operations of FIGS. 3A-3D, the determination in block 218 may therefore remain the same such that when the counter is greater than zero ("Yes" branch of decision block 218), the sequence of operations proceeds to block 220. However, when the counter is zero or less than zero (which, in this example, would correspond to the "No" branch of decision block 218), the sequence of operations proceeds to block 226. In light of the foregoing, it will be appreciated that the use of the term "counter" is not to be taken as an indication of some component that counts, but rather a number, flag, or other indicator that merely indicates the presence of syringe profiles in the dynamic syringe profile library 56.

Returning to flowchart 200, when there is a match for the selected syringe model in a syringe profile of the static syringe profile library 55 ("Yes" branch of decision block 226), the head processor 40 determines whether there is a match for the determined syringe diameter in the syringe profile (block 228). When there is a match for the determined syringe diameter in the syringe profile ("Yes" branch of decision block 228), the head processor 40 selects that syringe profile from the static syringe profile library 55 that includes the matching model and matching syringe diameter (block 230). However, when there is not a match for both the selected syringe model and the determined syringe diameter in a syringe profile of the static syringe profile library 55 ("No" branch of decision blocks 226 and 228, respectively), the head processor 40 indicates an error (block 232) and the sequence of operations may end. In response to selecting a syringe profile from the dynamic syringe profile library 56 (block 224) or selecting a syringe profile from the static syringe profile library 55 (block 230), the head processor 40 queries, in a human detectable form, whether the clinician wants to confirm the selection of the syringe profile to utilize in a flushing procedure (block 233). When the user does not confirm the selection of the syringe profile to utilize in the flushing procedure ("No" branch of decision block 233), the sequence of operations returns to block 212. However, when the user does confirm the selection of the syringe profile to utilize in the flushing procedure ("Yes" branch of decision block 233), the head processor 40 determines the volume of flush fluid required to flush the fluid line 26 during the flushing procedure (block 234), which can be based on clinician input or specified in the selected syringe profile.

After determining the volume of flush fluid for the flushing procedure (block 234), the head processor 40 may query the clinician in a human detectable form whether to use the same rate of infusion for the flushing procedure that the clinician specified for a previous infusion procedure (block 236). When the clinician indicates that a different rate is to be used for the flushing procedure ("No" branch of decision block 236), the head processor 40 determines the rate by analyzing data input and/or selections made by the clinician via operator interface 32 (block 238). Whether the clinician indicates that the same rate from the prior infusion procedure is to be used for the flushing procedure ("Yes" branch of decision block 236), or whether the head processor 40 determines the different rate to be used (block 238), the head processor 40 displays the flushing procedure settings to the clinician in human detectable form for confirmation (block 240). By way of example, the head processor 40 may display the total time required for the flushing procedure (which is specified by the clinician or calculated based upon the volume of flush fluid to infuse and the rate used for a previous infusion procedure), the rate for the flushing procedure (which is the same rate used for a previous infusion procedure or a new rate calculated from the volume of flush fluid to infuse and the clinician specified time required for the flushing procedure, or a new rate specified by the syringe profile), the total volume of flush fluid to deliver (which is specified by the clinician or specified by the syringe profile), and the program volume delivered identifier 60 on the display 30 of the head 12. When the clinician confirms the settings ("Yes" branch of decision block 242), the head processor 40 displays the flush procedure settings to the clinician for review, including the total time required for the flushing procedure, the total time remaining for the flushing procedure, the rate for the flushing procedure, the total volume of flush fluid to deliver, and the program volume delivered identifier 60 on the display of the head 12 (block 244), and starts the flushing procedure to flush the fluid line 26 to the patient 24 based on the above determined flushing procedure settings (block 246). As a consequence, to the extent a specified relationship is developed with the infusion procedure, it occurs after performance of the infusion procedure. Returning to block 242, when the clinician does not confirm the setting ("No" branch of decision block 242), the sequence of operations may return to block 234. After the flushing procedure is started, the head processor 40 continues to update and display the total time required for the flushing procedure, the total time remaining for the flushing procedure, the rate for the flushing procedure, the total volume of flush fluid to deliver, and the program volume delivered identifier 60 on the display 30 of the head 12.

Alternatively, it may be advantageous for the head processor 40 to select a syringe profile from only the dynamic syringe profile library 56. Changes to the static syringe profile library 55 require new head firmware 48, which is typically available only from the manufacturer of the syringe pump 10. However, the facility 102 can create new configuration data to replace the configuration data 50 and thus may more readily modify the syringe profiles in the dynamic syringe profile library 56. Moreover, the facility 102 can include, in the dynamic syringe profile library 56, some or all of the same syringe profiles found in the static syringe profile library 55, or modified versions thereof. As a consequence, the syringe pump 10 can be designed to only take into account the dynamic syringe profile library 56 and the syringe profiles therein. For example, and with respect to flowchart 200 of FIGS. 3A-3D, the head processor 40 may not perform the operation in block 218 and the sequence of operations may instead proceed directly from block 216 to block 220. Correspondingly, when there is not a match for the selected syringe model in a syringe profile of the dynamic syringe profile library 56 ("No" branch of decision block 220), or when there is not a match for the determined syringe diameter in an otherwise matching syringe profile in the dynamic syringe profile library 56 ("No" branch of decision block 222), the sequence of operations may proceed directly to block 232, bypassing blocks 226-230.

Figure 4:
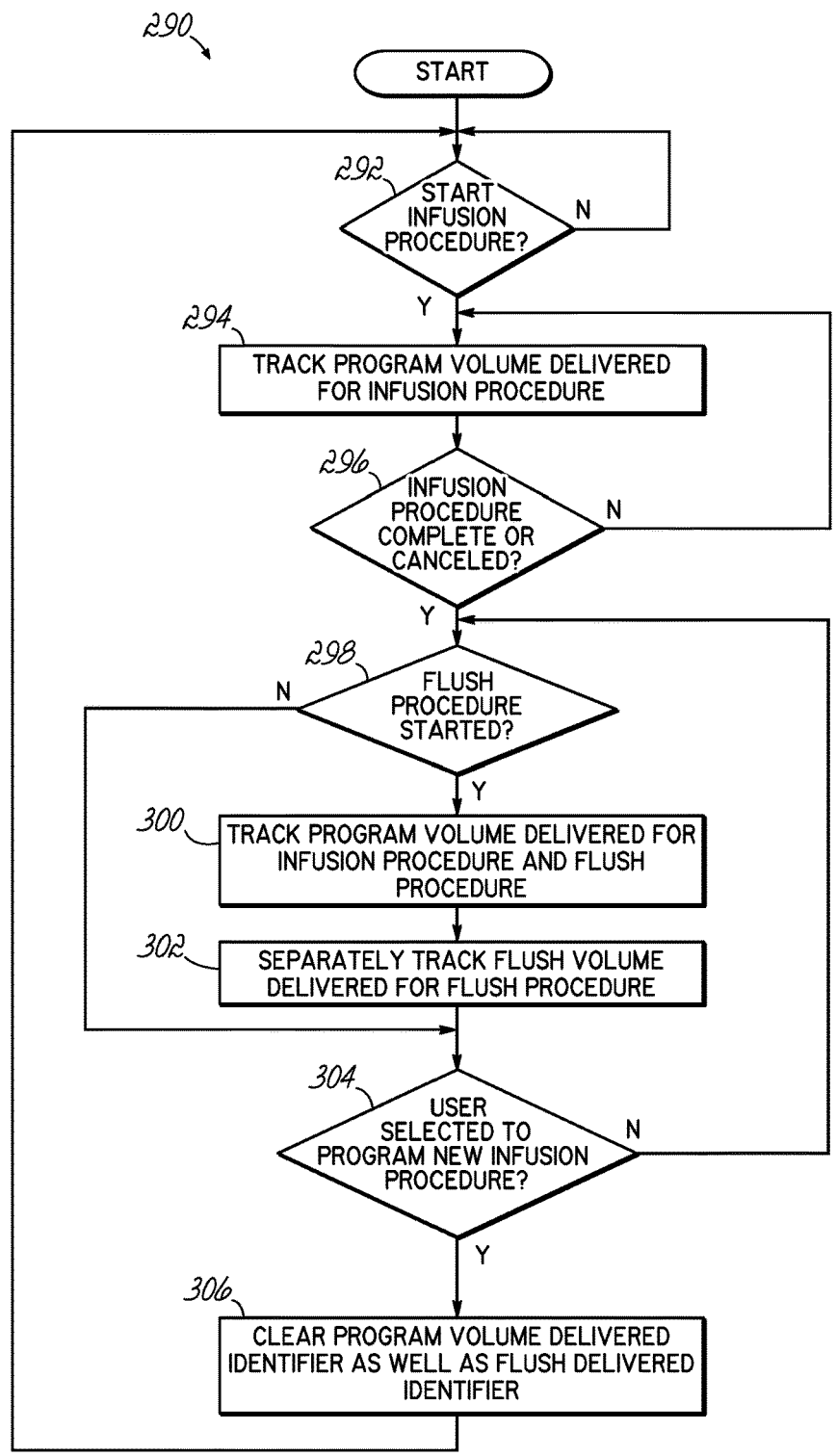
FIG. 4 is a flowchart illustrating a sequence of operations executable by the medical pump of FIG. 1 to track the volume of fluid delivered both during an infusion procedure and during a subsequent flushing procedure.

With reference to flowchart 290 of FIG. 4, this sequence of operations illustrates that the head processor 40 separately tracks the volume of fluid expelled both during an infusion procedure as well as during a subsequent flushing procedure in order to track the volume of medicament infused into the patient 24, as well as the volume of flushing fluid expelled during the flushing procedure. Initially the head processor 40 determines when an infusion procedure has begun (block 292). When an infusion procedure has not begun ("No" branch of decision block 292), the sequence of operations returns to block 292. However, when an infusion procedure has begun ("Yes" branch of decision block 292), the head processor 40 tracks the total volume of fluid expelled for the infusion procedure (block 294). During the infusion procedure, the head processor 40 may increment the program volume delivered identifier 60 about every half-second with the program volume delivered from the last half-second such that the head processor 40 keeps a running total of the volume of fluid expelled for an infusion procedure (block 294).

The head processor 40 also determines when an infusion procedure has completed or been canceled (block 296). When an infusion procedure has not completed and has not been canceled ("No" branch of decision block 296), the sequence of operations returns to block 294. However, when an infusion procedure has completed or been canceled ("Yes" branch of decision block 296), the head processor 40 determines whether the clinician has selected to start a flushing procedure (block 298). When the clinician has selected to start a flushing procedure ("Yes" branch of decision block 298), the head processor 40 adds to the total volume of fluid expelled during the infusion procedure the additional volume of flushing fluid expelled during the flushing procedure (block 300), and separately tracks the volume of flush fluid expelled by the flushing procedure (block 302). In accordance with one aspect of the present invention, the head processor 40 tracks the total volume of fluid expelled both during the infusion procedure and the flushing procedure with the program volume identifier 60 and tracks the volume of flushing fluid expelled with the flush volume delivered identifier 61 in a similar manner as described above.

In response to determining that a flushing procedure has not been started ("No" branch of decision block 298), or in response to tracking the total volume expelled during both an infusion procedure and a flushing procedure (block 300) as well as separately tracking the flushing fluid volume expelled for the flushing procedure (block 302), the head processor 40 determines whether a clinician has selected to program a new infusion procedure (block 304). When the clinician has not selected to program a new infusion procedure ("No" branch of decision block 304), the sequence of operations returns to block 298. When the clinician has selected to program a new infusion procedure ("Yes" branch of decision block 304), the head processor 40 clears the program volume delivered and flush volume delivered identifiers 60 and 61 (block 306) and the sequence of operations returns to block 292.

Figure 5:
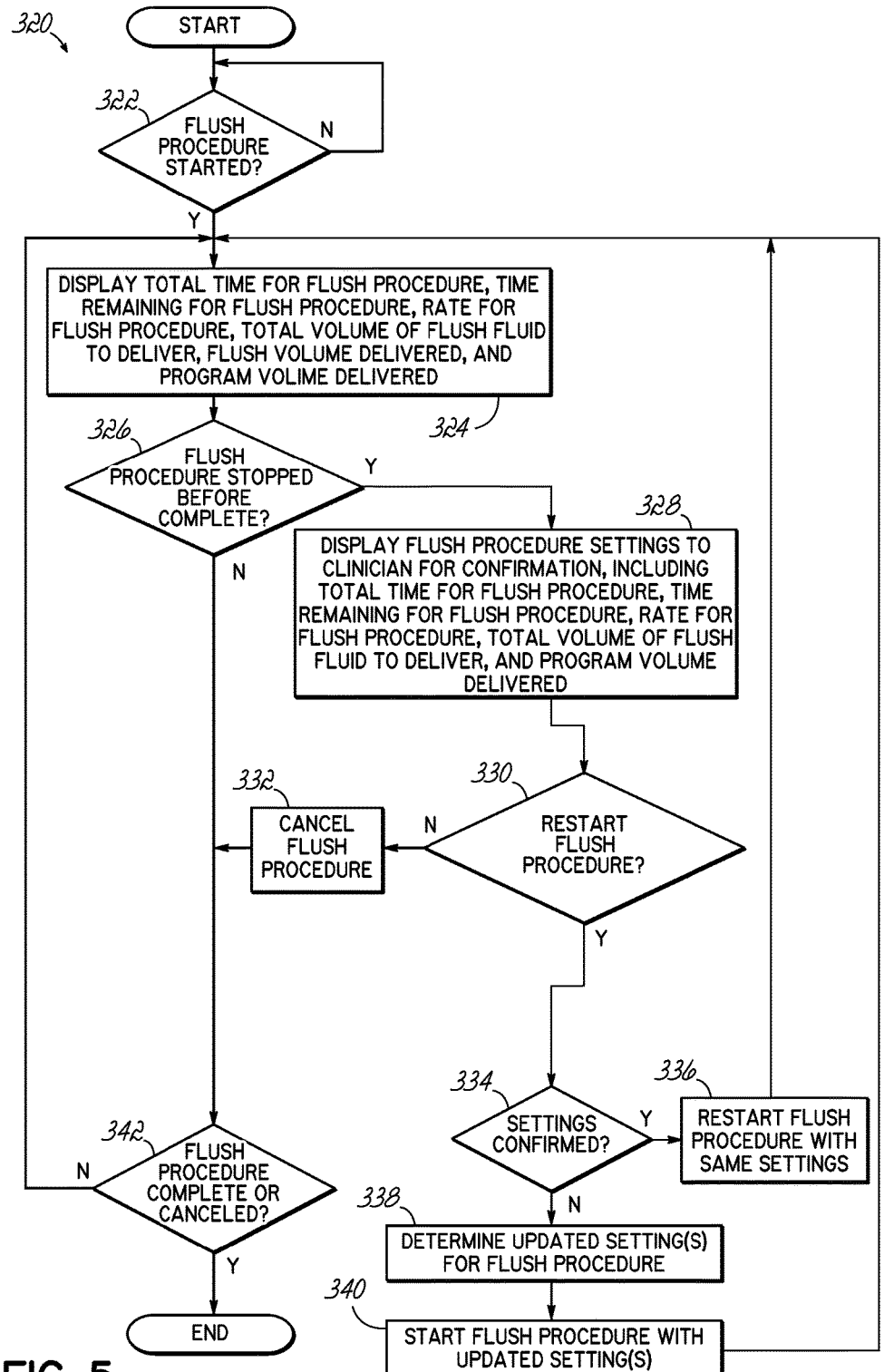
FIG. 5 is a flowchart illustrating a sequence of operations executable by the medical pump of FIG. 1 to automatically query in human detectable form whether a flushing procedure which has been interrupted is to be canceled or restarted, and to operate the medical pump accordingly.

With reference to flowchart 320 of FIG. 5, this sequence of operations illustrates that the head processor 40 displays the program volume delivered identifier 60 during a flushing procedure and further determines whether a flushing procedure has been paused, restarted, and/or changed. The head processor 40 determines whether a flushing procedure has been started (block 322). When the flushing procedure has not been started ("No" branch of decision block 322), the sequence of operations may return to block 322. However, when the flushing procedure has been started ("Yes" branch of decision block 322), the head processor 40 displays, in human detectable form, the total time for the flushing procedure, the time remaining for the flushing procedure, the rate for the flushing procedure, the total volume of the flushing fluid to deliver, the volume of flushing fluid expelled from flush volume delivered identifier 61, and the program volume delivered identifier 60 (block 284). The head processor 40 may display those values on the display 30 and update those values during the flushing procedure.

At block 326, the head processor 40 detects if the flushing procedure has been stopped, and if so, whether it has been stopped before it was completed (e.g., it has been paused). If the flushing procedure has been stopped before it has completed ("Yes" branch of decision block 326), the head processor 40 displays flush procedure settings to the clinician for confirmation (block 328). These flush procedure settings include the total time for the flushing procedure, the time remaining for the flushing procedure, the rate for the flushing procedure, the flushing volume expelled based on the flushing volume delivered identifier 61, and the program volume delivered identifier 60. The head processor 40 also automatically queries the clinician (not shown) in human detectable form (such as on display 30 or aurally as in the case of the automatic query whether to perform a flush procedure described above) whether to restart the flushing procedure (block 330). When the clinician has selected not to restart the flushing procedure ("No" branch of decision block 330), the flushing procedure is canceled (block 332). However, when the clinician has selected to restart the flushing procedure ("Yes" branch of decision block 330), the head processor 40 determines whether the clinician has confirmed the settings previously displayed (block 334). When the clinician has confirmed the settings previously displayed (e.g., the settings to restart the flushing procedure are the same as previously used) ("Yes" branch of decision block 334), the head processor 40 restarts the flushing procedure with the same settings (block 336) and the sequence of operations returns to block 324. However, when the clinician has not confirmed the settings for the flushing procedure ("No" branch of decision block 334), the clinician is queried in human detectable form at block 338 for updated settings for the flushing procedure and the head processor 40 restarts the flushing procedure with the updated settings (block 340). The sequence of operations then returns to block 324.

Referring back to block 326, if the head processor 40 determines that the flushing procedure has not been stopped before it has completed ("No" branch of decision block 326), the sequence of operations proceeds to block 342. Similarly, if the flushing procedure has been canceled (block 322), the sequence of operations proceeds to block 342. At block 342, the head processor 40 determines whether the flushing procedure has been completed or canceled. When the flushing procedure has not completed and has not been canceled ("No" branch of decision block 342), the sequence of operations returns to block 324. However, when the flushing procedure has completed or has been canceled ("Yes" branch of decision block 342), the sequence of operations ends.

While the present invention has been illustrated by a description of an embodiment of the thereof, and the embodiment has been described in considerable detail, it is not the intention of the applicants to restrict or in any way limit the scope of the appended claims to such detail. Additional advantages and modifications will readily appear to those having ordinary skill in the art. By way of example, while the embodiment shown herein is of a medical pump in the form of a particular syringe pump 10 configured to perform all of the various features of the present invention, it will be appreciated that other forms or types of medical pumps may advantageously be configured to implement those features. Further, a medical pump may advantageously be configured to implement fewer of the features. Further, while the response to the automatic queries is shown as being implemented at or on the medical pump, it will be appreciated that the automatic queries and responses may be implemented remotely via the network interface 80 or wireless network interface 84 and/or the network 76. Other alternative hardware and/or software environments may be used than those shown herein. Similarly, a person having ordinary skill in the art will appreciate that any of the blocks of the above flowcharts may be deleted, augmented, made to be simultaneous with another, combined, or be otherwise altered in accordance with the specific needs of the medical pump and the patient or facility needs in the use of that medical pump. In that regard, performance of an infusion procedure may actually involve performing only part of such a procedure, after which the automatic query for a flushing procedure occurs. Moreover, the head processor 40 may load the list of syringe models for syringe profiles in the memory 42 and memory 66, or just those of memory 66, in response to the clinician navigating to a screen to select a syringe profile for an infusion procedure or flush procedure. The invention in its broader aspects is therefore not limited to the specific details, representative apparatus and method, and illustrative example shown and described. Accordingly, departures may be made from such details without departing from the spirit or scope of the general inventive concept.

Having described the invention, what is claimed is:

1. A method of flushing a fluid line with a medical pump configured to execute a flushing procedure subsequent to an infusion procedure, the method comprising:
   providing an alarm corresponding to the conclusion of the infusion procedure;
   receiving an acknowledgement of the alarm;
   automatically querying in human detectable form whether to proceed with the flushing procedure in response to receiving the acknowledgment, the flushing procedure lacking a specified relationship with the infusion procedure until after performance of the infusion procedure; and
   starting the flushing procedure after conclusion of the infusion procedure based, at least in part, upon receiving input in response to the automatic query.

2. The method of claim 1, further comprising:
   silencing an alarm, and
   wherein:
      the alarm indicates the completion of the infusion procedure, and
      automatically querying in human detectable form whether to proceed with the flushing procedure occurs in response to the silencing of the alarm.

3. A medical pump comprising:
   at least one processing unit; and
   a memory containing program code configured to, when executed by the at least one processing unit:
      provide an alarm corresponding to the conclusion of the infusion procedure;
      receiving an acknowledgement of the alarm; and
      automatically query in human detectable form whether to proceed with a flushing procedure in response to receiving the acknowledgment, the flushing procedure lacking a specified relationship with the infusion procedure until after performance of the infusion procedure, and
   wherein the memory containing program code is further configured to start the flushing procedure after conclusion of the infusion procedure based, at least in part, upon receiving input in response to the automatic query.

4. A method of flushing a fluid line with a medical pump configured to execute a flushing procedure, the method comprising:
performing the flushing procedure with a flushing fluid to flush the fluid line;
stopping the flushing procedure before it is completed;
in response to stopping the flushing procedure before it is completed, displaying a setting for the flushing procedure and automatically querying in human detectable form whether to restart the flushing procedure after it has been stopped; and
restarting the flushing procedure in response to a determination to restart the flushing procedure, wherein the determination to restart the flushing procedure is in response to the automatic query.

5. The method of claim 4 further comprising restarting the flushing procedure with at least one altered setting.

6. The method of claim 4 further comprising canceling the flushing procedure.

7. A medical pump comprising:
at least one processing unit; and
a memory containing program code configured to, when executed by the at least one processing unit;
perform a flushing procedure with a flushing fluid to flush a fluid line;
stop the flushing procedure before it is completed;
in response to stopping the flushing procedure before it is completed, display a setting for the flushing procedure and automatically query in human detectable form whether to restart the flushing procedure after it has been stopped, and
wherein the memory containing program code is further configured to restart the flushing procedure in response to a determination to restart the flushing procedure, wherein the determination to restart the flushing procedure is in response to the automatic query.

8. The medical pump of claim 7, the program code further configured to restart the flushing procedure with at least one altered setting.

9. The medical pump of claim 7, the program code further configured to cancel the flushing procedure.

10. A method of tracking a volume of medicament infused by a medical pump configured to expel medicament into a fluid line, the method comprising:

determining a volume of medicament expelled into the fluid line during an infusion procedure;
increasing the volume of medicament expelled by an amount equal to a volume of flushing fluid expelled into the fluid line during a flushing procedure after conclusion of the infusion procedure; and
periodically updating during the flushing procedure a total volume of medicament expelled by summing the volume of medicament expelled into the fluid line during the infusion procedure and the volume of flushing fluid expelled into the fluid line during the flushing procedure.

11. The method of claim 10 further comprising displaying the total volume of medicament infused.

12. The method of claim 10 further comprising separately determining the total volume of flushing fluid expelled during the flushing procedure.

13. The method of claim 12 further comprising separately displaying both the total volume of medicament infused and the total volume of flushing fluid expelled.

14. A medical pump comprising:
at least one processing unit; and
a memory containing program code configured to, when executed by the at least one processing unit;
determine a volume of medicament expelled into a fluid line during an infusion procedure; and
increase the volume of medicament expelled by an amount equal to a volume of flushing fluid expelled into the fluid line during a flushing procedure after conclusion of the infusion procedure
periodically updating during the flushing procedure a total volume of medicament expelled by summing the volume of medicament expelled into the fluid line during the infusion procedure and the volume of flushing fluid expelled into the fluid line during the flushing procedure.

15. The medical pump of claim 14, the program code further configured to display the total volume of medicament infused.

16. The medical pump of claim 14, the program code further configured to separately determine the total volume of flushing fluid expelled during the flushing procedure.

17. The medical pump of claim 14, the program code further configured to separately display both the total volume of medicament infused and the total volume of flushing fluid expelled.

* * * * *